United States Patent [19]
Khamis

[11] Patent Number: 5,470,562
[45] Date of Patent: Nov. 28, 1995

[54] COSMETIC PIGMENT COATING AND METHOD OF APPLICATION IN NAIL POLISH

[75] Inventor: Adel A. Khamis, Belleville, N.J.

[73] Assignee: Tevco, Inc., South Plainsfield, N.J.

[21] Appl. No.: 206,248

[22] Filed: Mar. 4, 1994

Related U.S. Application Data

[60] Continuation of Ser. No. 901,524, Jun. 19, 1992, abandoned, which is a division of Ser. No. 689,379, Apr. 22, 1991, Pat. No. 5,133,966, which is a continuation-in-part of Ser. No. 501,677, Mar. 29, 1990, abandoned.

[51] Int. Cl.⁶ .......................... A61K 7/043; B23B 27/00
[52] U.S. Cl. .................. 424/61; 106/178; 106/262; 106/504; 106/505; 424/401
[58] Field of Search .............. 424/401, 61; 106/178, 106/262, 266, 504, 505, 902, 903, 904; 428/402, 403, 407

[56] References Cited

U.S. PATENT DOCUMENTS

| | | | |
|---|---|---|---|
| 3,864,294 | 2/1975 | Busch, Jr. | 106/266 X |
| 4,421,565 | 12/1983 | Dibella | 106/262 X |
| 4,601,757 | 7/1986 | Brown et al. | 106/183 |
| 4,634,471 | 1/1987 | Foye et al. | 106/262 |
| 4,740,370 | 4/1988 | Faryniarz et al. | 424/61 |
| 4,832,944 | 5/1989 | Socci et al. | 424/61 |
| 4,897,261 | 1/1990 | Yamazaki et al. | 424/61 |
| 4,952,245 | 8/1990 | Iwano et al. | 106/404 |
| 4,956,018 | 9/1990 | Kranz et al. | 106/401 |
| 4,986,853 | 1/1991 | Kieser | 106/504 |
| 5,093,108 | 3/1992 | Pappas et al. | 424/61 |
| 5,143,723 | 9/1992 | Calno et al. | 424/63 |
| 5,174,996 | 12/1992 | Weber et al. | 424/401 |

*Primary Examiner*—John C. Bleutge
*Assistant Examiner*—Robert H. Harrison
*Attorney, Agent, or Firm*—Handal & Morofsky

[57] ABSTRACT

A pigment coating formulation for use in cosmetics and method of application to pigments is disclosed. The combination of a carboxylic acid and a metal salt of a carboxylic acid provides for an improved coating and advantages in pigment suspension, dispersion and product stability in nail polish.

15 Claims, No Drawings

COSMETIC PIGMENT COATING AND METHOD OF APPLICATION IN NAIL POLISH

CROSS-REFERENCE TO RELATED APPLICATIONS

This application is a continuation of application Ser. No. 07/901,524, filed Jun. 19, 1992, now abandoned, which was division of application Ser. No. 07/689,379, filed Apr. 22, 1991, which issued to Pat. No. 5,133,966, on Jul. 28, 1992. Application Ser. No. 07/689,379, was a continuation-in-part of application Ser. No. 501,677, filed Mar. 29, 1990, now abandoned.

TECHNICAL FIELD

The present invention relates to the field of cosmetics and the incorporation of pigments into a nail polish vehicle, or base.

BACKGROUND

Cosmetics in one form or another have been around since prehistoric times. Body paint, whether for religious, ritual or ornamental purposes, is an obvious example.

Recorded use of cosmetics dates back 6,000 years in Egypt. Ancient hieroglyphics and portraits reveal extensive accentuation of eyes through the use of make-up. Furthermore, eye make-up preparations including kohl, for lashes and brows, and colored eye shadows have been found in ancient tombs. Dyes were also used on fingers and toes for ornamental purposes.

Powders and sticks of talc, charcoal, and rouge preparations were in use in ancient Greece. The use of the cosmetics spread to the Middle Eastern areas, many of which may have already learned of cosmetics from the Chinese, and into Rome, where extravagant use often required slave-cosmeticians for proper application.

Use of cosmetics waxed and waned, reaching a peak in the Renaissance when both men and women made lavish use of cosmetic preparations.

The twentieth century brought another boom to make-up as the "pace of the times" was increasing due to improved and faster communications and travel. Distant and foreign styles, including cosmetic preparations and applications, spread swiftly and bred more change which in turn spread elsewhere.

The fashion industry became spotlighted by the various medias and advertisements promoted make-up creating an enormous market. The scientific preparation of cosmetics have been fostered and extolled. The market continues to grow as new products and brand names are constantly introduced.

The large market created also insures competition for that market. Product comparison is inevitable and product appearance is one very important basis of comparison. As cosmetics appeal to vanity and the purpose of cosmetics is to enhance personal appearance, the product appearance, along with packaging, etc., is an important factor in consumer acceptance and product success.

Preparations such as nail polish are presented in a manner displaying the product itself, through clear containers or package windows. Preparations such as these contain pigments mixed and suspended in various solvents or make-up bases. Should the incorporated pigments float, settle, striate or separate the product's appearance is adversely affected. A product's shelf-life is dependent upon avoiding these occurrences over time.

Many coatings and methods of treating pigments have been proposed to improve the dispersion and suspension characteristics of nail-polish pigments. Coatings based on lecithin and associated fatty acids such as palmitic, stearic and oleic acids or their salts have been applied to increase pigment dispersion and hydrophobicity. Some examples of an extensive field of research are U.S. Pat. Nos. 4,710,375 (Takasuka et al.), Reissue 31,602 (4,375,989 Makinnen),, 2,068,066 (O'Brien), 1,946,052 (Baldwin) and 1,894,168 (Gardner). Efforts to improve the performance of these dispersion agents include some exotic proposals, for example, use of a phosphorylated fatty acid, U.S. Pat. No. 3,343,974 (Faulkner). Some of the patents in this field relate to paint, and their end products are not suitable for use on humans.

A major drawback arising from the use of fatty acids or their salts is that an adequately uniform coating of the pigments is not achieved: This non-uniformity of the coating can result in agglomeration or floatation of the pigments in subsequent processing, yielding an unacceptable end product.

It has also been proposed to use a silicone coating in a method which calls for the tumbling of the pigment while spraying the pigment with silicone in a 2% solution with a carrier, and then heating the pigment, in the presence of a catalyst, to approximately 70° C. in order to cure the silicone.

This method also suffers from the problems of non-uniformity and complete curing of the silicone does not occur. Untreated silicone can form a layer on top of the liquid make-up. Additionally, uncured silicone can react with moisture and alcohol forming hydrogen gas.

Other drawbacks inherent with the silicone coating process are a reduced gloss of the finished product and reduced hiding power of the pigment. The reduced hiding power can result in requiring up to 25% more pigment in the cosmetic. An increase in pigment further increases the problems associated with non-uniformly coated pigments and uncured silicone on the pigments.

In summary, there has been a longfelt need for a simple system to improve the dispersibilty of pigments to be used in nail polish. In particular, there is a need to provide a system which can be used to pre-treat the pigment before grinding, will coat newly exposed surfaces of the pigment effectively during the grinding process, and can reduce the need for dispersion agents in the end-product nail polish. It is furthermore important that any such pigment treatment system not affect the performance of the pigment, notably its hiding power and color.

SUMMARY OF THE INVENTION

The invention is intended to provide a remedy and to provide a pigment pretreatment composition which makes important progress in satisfying this longfelt need for a simple and effective system. It solves the problems of achieving an adequately uniform coating of the pigment and avoids problems associated with free silicone mixed with the pigment. The inventive method achieves a uniform coating of the pigments not achieved with the previous lecithin, fatty acid or metallic soap treatments.

Broadly stated, the present invention uses both carboxylic acids and carboxylic acid salts with a resin carrier in a buffered coating process that yields a hydrophobic coating with increased dispersion characteristics in nail polish vehicles. This novel and uniform coating provides the important benefits of preventing agglomeration, settling, floating of the pigment or separation. Surprisingly, these advantages are obtained without affecting the hiding power of the pigments or gloss of the nail polish products. More specifically, the invention provides, in one aspect a nail polish pigment coating formulation for pre-treating nail polish pigment to improve the dispersibility, suspensibilty and stability of the pigment in a nail polish, the formulation comprising, in relative proportions by weight:

one part of a hydrophobic carboxylic acid having from 3 to 18 carbon atoms;

from 0.1 to 10 parts by weight of a non-toxic metal salt of a carboxylic acid also having from 3 to 18 carbon atoms; and from 0.5 to 100 parts based on the combined weight of said acid and said acid salt of a carrier resin; and sufficient organic solvent to wet the pigment.

Some preferred proportions are from 0.75 to 1.5 parts of carboxylic acid salt per part of acid, and from 1.0 to 10.0 parts of carrier resin per combined part of acid and salt. The quantity of solvent used may be Just enough to formulate the coating composition or to wet the intended quantity of pigment, for example as low as one-third the weight of pigment. A reasonable maximum is about ten times the weight of pigment with up to two times being preferred.

BEST MODE FOR CARRYING OUT THE INVENTION

In the inventive method a coating material mixture is prepared comprising a carboxylic acid and a metal salt of the same or a similar acid, in weight amounts of the same order of magnitude, a carrier resin and a solvent. The acid and the salt make up 10 to 50 weight percent of the mixture for optimum conditions but the percentage may vary widely as this solution is in turn added to the pigment grinding solvent which may be similar to the mixture solvent. The carrier resin may be an alkyd resin and should be present in an amount on the same order of magnitude as both the carboxylic acid and salt combined.

The carboxylic acid used is preferably a 3 to 18 carbon fatty acid and the salt is also preferably of a 3 to 18 carbon acid. A relatively straight chain carboxylic acid is preferable to a highly branched structure.

A monovalent or bivalent metal salt such as a sodium, potassium or calcium salt is preferable although any reasonably non-toxic salt, regardless of the valency of the metal, may be used. Adjustment of the amount of salt, in molar terms, may be necessary between different valency salts. Put more broadly, the metallic cation can be selected from the group consisting of alkali and alkaline earth metals, ammonium and aluminum.

The coating material mixture is added to the pigment grinding solvent in an amount of 0.1 to 10.0 weight percent of the pigment to be treated and thoroughly mixed in. The pigment, totaling 10 to 50 weight percent of the grinding solvent-pigment mixture, is added and completely mixed.

The grinding mixture is allowed 5 to 30 hours sitting time. Less time results in a usable but less effectively coated pigment while the point of diminishing returns in pigment treatment is passed at over 30 hours. No heating is necessary in this process.

As an acid-salt combination is used, the coating time for the pigments can be made as long as desirable, allowing for all-day or overnight treatments. This is due to the buffering action of the acid-salt combination, keeping the pH of the mixture regulated. The liquid phase coating operation, combined with the self-regulated pH and time available for coating results in a highly uniform coating.

Nitrocellulose is dissolved in the grinding mixture and mixed, followed by the addition of a resin and solvents and further mixing. The grinding mixture is now ready to be milled.

The mixture is to be ground to at least 8+ on the Hegman scale. The ground mixture is now a pigment paste to be used in the formulation of cosmetic products.

As the coated pigment is ground, the coating extends to newly exposed pigment surfaces created by the milling process. This coating process is much more effective with a pigment that has been given adequate sitting time with the carboxylic acid—salt combination and therefore has attained a pre-grinding coating. Lack of sitting time or treatment after milling results in a less uniform coating.

The uniformity and hydrophobicity of the coating allows for the significant reduction in the use of stearalkonium hectorite, sold under the trade mark Bentone (TM), a suspension aid in nail polish formulation. This is an important improvement, as Bentone (TM) can lead to overgelling of a nail polish product by aging, can reduce gloss of the product and can lead to syneresis, oil separation.

A preferred embodiment of the inventive method of the present invention comprises a pigment coating produced by a process of making cosmetic pigment material for use in nail polish comprising the steps of:

a) preparing a cosmetic pigment coating formulation by:
   i) combining a carboxylic acid with a metal salt of a carboxylic acid, an alkyd resin and a solvent; and
   ii) mixing together said carboxylic acid, said metal salt, said resin and said solvent thoroughly;

b) mixing said cosmetic pigment coating formulation with a pigment paste solvent;

c) adding a pigment to be coated to the mixture of said cosmetic pigment coating formulation and pigment paste solvent;

d) mixing said pigment, said cosmetic pigment coating formulation and said pigment paste solvent to make a preliminary mixture;

e) aging said preliminary mixture for a time sufficient to enable a preliminary coating by said carboxylic acid around said pigment;

f) adding nitrocellulose and a carrier resin to the aged mixture of said pigment, said coating formulation and said pigment paste solvent;

g) mixing together said nitrocellulose, said carrier and the aged mixture to create a mixed combination of nitrocellulose, carrier resin and said aged mixture; and h) milling the mixed combination of nitrocellulose, carrier resin and said aged mixture.

The calcium salt, calcium octoate, is commercially available usually in solution in mineral spirits, whereas a toluene solution of the salt would be preferable.

The carrier resin could be one or more of the following: an acrylates copolymer; a styrene acrylate copolymer; a urethane elastomer, for example Spenlite L90-20H, Spencer-Kellog Co.; a non-oxidizing alkyd resin for example Cellokyd 1146T, Cellomer Co.; a polyester resin for example CV 160 Cellomer Co.; a polyester hard resin, for example, Aroplaz 642, Spencer Kellogg Co.; a hydrocarbon resin, for example Cellolyn 102 Hercules Inc.; or a toluenesulfonamide formaldehyde resin.

An effective coating mixture formulation can be prepared in a composition comprising 12.5 per cent of an eight carbon, saturated carboxylic acid, 12.5 per cent of a solution of a calcium salt of the carboxylic acid (5% calcium in mineral spirits), 25 per cent of a carrier resin and 50 per cent toluene.

In practicing preferred embodiments of the process of this invention, the coating formulation ingredients are mixed together at moderate speed, i.e. 700 rpm, for approximately twenty minutes. The coating formulation is mixed with a pigment paste solvent, preferably a toluene-butyl acetate combination, or ethyl, propyl or butyl acetate alone or in combination with each other or toluene, in the range of 0.5 to 5.0 weight per cent of coating formulation based on the weight of the solvent, although any percentage up to 10.0 weight per cent can be used. A point of diminishing returns is reached by the 10.0 weight per cent figure (10% of the solvent weight, that is) for the proposed amount of pigment to be added.

Pigment, in the amount of 50 to 200 weight per cent of the coating mix-solvent mixture, is mixed in by slow addition such as sprinkling while mixing followed by moderate to high speed mixing such as at 70 to 1500 rpm, for an additional 20 minutes.

Additional solvents, resins, and suspension aids weighing on the same order of magnitude as the treated pigment, are added to complete the pigment paste mixture ingredients and then thoroughly mixed and milled to where the grind is at least 8+ on the Hegman scale. Such additional materials include the previously mentioned solvents, stearalkonium hectorite, nitrocellulose, camphor, dibutyl phthalate, benzophenone and resins such as those listed above. Adequate sitting time of 12 to 24 hours to allow the pigment to become wetted by the coating mixture formulation should be given before milling.

Any conventional mill known to be suitable for the purpose can be used to grind the coated pigment paste. Examples of such mills are: stainless steel ball mills, two- or three roller mills, bead mills, pebble mills and the like. In general, three-roller mills require one third the amount of solvent, while two roller mills require none.

The pigment paste is then used in other solutions to produce the desired nail polish shade.

Pigment pastes for titanium dioxide, iron oxides, other pigments such as ferric ammonium ferrocyanide and organic pigments may be prepared, with substantial end-product and processing benefits, using the pigment coating formulations and methods of this invention. However, primary benefits are obtained from pretreating inorganic rather than organic pigments. Inorganic pigments have a high specific gravity and are therefore prone to settle out.

Extenders and pearlescent material such as talc, mica and bismuth oxychloride may also be treated and rendered into pastes for cosmetic preparations. These pigment pastes may be mixed to obtain desired shades and suspended in a normal suspension base of toluene, butyl acetate and ethyl acetate as is known in the field to produce a nail polish product. The nail polish product may include 5 to 40 per cent pigment paste for typical products.

Nail polishes using materials coated with the acid-salt formulation have shown advantages including: higher gloss; higher hiding capability, better suspension in a centrifuge; no hydrogen production; decreased syneresis; decreased amount of Bentone required for suspension; better brushability and flow of the product.

Treated materials used in the polishes include: titanium dioxide; dye and color red #6; dye and color red #7; dye and color red #34; dye and color red #36, dye and color yellow #5, black iron oxide, red iron oxide, iron blue, bismuth oxychloride, and guanine (a pearlescent pigment).

Some specific examples of the process and compositions of this invention will now be described, by way of illustration of the concepts of the invention:

EXAMPLE 1

Using the methods described above, a white nail polish suspension is prepared in stages:

Stage 1: Pigment additive coating formulation.

A pigment pretreatment formulation or coating mix is prepared by blending the following ingredients in the proportions indicated:

|  | Weight % |
| --- | --- |
| Calcium Octoate (5% Ca metal in mineral spirits) | 12.5 |
| Octoic acid (2 Ethylhexoic Acid) | 12.5 |
| Carrier resin | 25.0 |
| Toluene | 50.0 |
| Total | 100.00 |

Stage 2: Titanium dioxide paste formulation

This coating formulation is used as an additive in the preparation of a paste. The foregoing coating mix (the additive) is thoroughly mixed with solvent in the following proportions:

|  | Weight % |
| --- | --- |
| Toluene | 4.07 |
| Butyl acetate | 35.26 |
| Additive | 1.63. |

Into this mixture is sprinkled while mixing, preferably at 700 rpm:

Titanium dioxide 41.19.

The resultant dispersion is allowed to stand and set for about 24 hours, after which the following ingredients are added:

|  | Weight % |
| --- | --- |
| Butyl acetate | 2.25 |
| Ethyl acetate | .56 |
| Toluene | 2.25 |
| Stearalkonium hectorite | .43 |
| RS Nitrocellulose (¼ s) | 7.86 |
| Camphor | 1.86 |
| Toluenesulfonamide/formaldehyde resin (80%) | 2.64 |
| Total of all ingredients: | 100.00 |

This titanium dioxide pigment paste mixture is then milled to a grind of at least 8+ on the Hegman scale and used in Stage 3.

Stage 3: Preparation of Nail Polish Suspension

The titanium dioxide pigment paste mixture from stage 2 is thoroughly mixed to disperse it in a suspension base with the following composition:

|  | Weight % |
|---|---|
| Toluene | 25.78 |
| Titanium Dioxide Paste from Stage 2 | 22.00 |
| Butyl Acetate | 13.38 |
| Nitrocellulose | 9.53 |
| Ethyl Acetate | 8.92 |
| Toluenesulfonamide Formaldehyde Resin | 8.40 |
| Dibutyl Phthalate | 6.00 |
| Isopropyl Alcohol | 4.26 |
| Camphor | 1.38 |
| Stearalkonium Hectorite | .25 |
| Benzophenone 1 | .10 |
| Total | 100.00 |

EXAMPLE 2: Red Iron Oxide Formulation

The procedure of Example 1 is followed to produce a red iron oxide nail polish suspension. A similar coating formulation is used in Stage 1. In Stage 2 the following proportions are used for preparation of the pigment paste:

|  | Weight % |
|---|---|
| Toluene | 3.25 |
| Butyl Acetate | 39.65 |
| Additive | 1.39 |
| Iron oxide | 35.00 |
| Butyl Acetate | 2.45 |
| Ethyl Acetate | .61 |
| Toluene | 2.45 |
| Stearalkonium Hectorite | .47 |
| RS Nitrocellulose (¼ s) | 8.74 |
| Camphor | 2.09 |
| Toluenesulfonamide formaldehyde resin (80%) | 3.90 |
| Total | 100.00 |

To prepare a red nail polish suspension, the following formulation is used:

|  | Weight % |
|---|---|
| Toluene | 27.39 |
| Iron Oxide Paste | 19.99 |
| Nitrocellulose (30% IPA wet) | 15.55 |
| Butyl Acetate | 10.52 |
| Ethyl Acetate | 8.83 |
| Toluenesulfonamide formaldehyde resin (80% in BAc) | 8.61 |
| Dibutyl Phtalate | 6.19 |
| Camphor | 1.88 |
| Stearalkonium Hectorite | 1.04 |
| Total of all ingredients: | 100.00 |

EXAMPLE 3: Blue Ferric Ammonium Ferrocyanide Formulation

The procedure of Example 1 is followed to produce a blue ferric ammonium ferrocyanide nail polish suspension. A similar coating formulation is used in Stage 1. In Stage 2 the following proportions are used for preparation of the pigment paste:

|  | Weight % |
|---|---|
| Toluene | .97 |
| Butyl Acetate | 12.21 |
| Additive | .64 |
| Ferric ammonium ferrocyanide | 10.78 |
| Butyl Acetate | 31.25 |
| Ethyl Acetate | .24 |
| Stearalkonium Hectorite | .19 |
| RS Nitrocellulose (¼ s) | 5.84 |
| Camphor | .13 |
| Toluenesulfonamide formaldehyde resin (80% in Bu Ac) | 32.36 |
| Dibutyl Phthalate | 5.39 |
| Total of all ingredients | 100.00 |

This ferric ammonium ferrocyanide paste of is used to prepare a ferric ammonium ferrocyanide dispersion or suspension with the following ingredients:

|  | Weight % |
|---|---|
| Toluene | 25.49 |
| Ferric ammonium ferrocyanide paste | 25.85 |
| Nitrocellulose (30% IPA wet) | 15.61 |
| Butyl Acetate | 20.44 |
| Ethyl Acetate | 5.73 |
| Toluenesulfonamide formaldehyde resin (80% in Bu Ac) | 2.01 |
| Dibutyl Phthalate | 2.68 |
| Camphor | .87 |
| Stearalkonium Hectorite | 1.22 |
| Benzophenone-1 | .10 |
| Total of all ingredients | 100.00 |

EXAMPLE 4: Red Iron Oxide Formulation

The procedure of Example 1 is followed to produce a red iron oxide nail polish suspension. The coating formulation used in Stage 1 is as follows:

|  | Weight % |
|---|---|
| Calcium Octoate (5% Ca metal in mineral spirits) | 0.15 |
| Octoic acid (2 Ethylhexoic Acid) | 0.15 |
| Carrier resin | 1.77 |
| Toluene | 2.96 |
| Butyl acetate | 47.33 |

In Stage 2 the following ingredients are added, in the manner described in Example 1 to the above coating formulation:

|  | Weight % |
|---|---|
| Red iron oxide pigment | 26.25 |
| Butyl Acetate | 11.23 |
| Stearalkonium Hectorite | 0.62 |
| Nitrocellulose | 6.46 |
| Camphor | 1.14 |
| Toluenesulfonamide formaldehyde resin (80%) | 1.94 |

-continued

|  | Weight % |
|---|---|
| Total | 100.00 |

To prepare a red nail polish dispersion or suspension, following the method of Example 1, the following formulation is used:

| | |
|---|---|
| Toluene | 27.01 |
| Iron Oxide Paste | 24.38 |
| Nitrocellulose (30% IPA wet) | 15.08 |
| Butyl Acetate | 10.28 |
| Ethyl Acetate | 6.40 |
| Toluenesulfonamide formaldehyde resin (80% in BAc) | 8.71 |
| Dibutyl Phtalate | 6.19 |
| Camphor | 0.86 |
| Stearalkonium Hectorite | 1.09 |
| Total of all ingredients: | 99.99 |

EXAMPLE 5: Bismuth Pearlescent Dispersion

The procedure of Example 1 was repeated except that bismuth oxychloride was used in place of titanium dioxide, in the following proportions, to provide a bismuth pearlescent suspension:

| | Weight % |
|---|---|
| Bismuth oxychloride (BWD) | 99.54 |
| Additive (Ex. 1, Stage 1) | .46 |
| Total | 100.00 |

EXAMPLE 6: Mica or Timica Pearlescent Dispersion

The procedure of Example 1 was repeated except that mica or timica was used in place of titanium dioxide, in the following proportions, to provide a mica or timica pearlescent suspension:

| | |
|---|---|
| Mica or Timica | 96.91 |
| Additive | 3.81 |
| Total | 100.00 |

The following shades of nail polish have been made for stability tests against a conventional commercially available silicone-treated titanium dioxide, iron oxide and ferric ammonium ferrocyanide, as a control but which does not contain the inventive additive. The white, colored and pearlescent nail polish suspensions produced by the foregoing Examples are used in nail polish formulations, in various proportions, to produce a variety of tints. The proportions of ingredients used in the foregoing Examples have been carefully chosen to be balanced so that the suspensions produced can readily be used in a modular manner in preparing the end-product nail polishes with complex colors from a set of base colors.

The following Table 1 provides examples of some advantageous nail polish formulations that can be made up using the pigment dispersions from the preceding Examples. The suspension base recited below comprises a selection of ingredients from the group comprising n-butyl acetate, ethyl acetate, toluene, polyester resin, benzophenone, camphor, nitrocellulose, stearalkonium hectorite, dibutyl phthalate and isopropyl alcohol.

A full analysis of the composition of these novel nail polish formulations is set forth in Table 2, following Table 1.

TABLE 1

| Weight % | | | |
|---|---|---|---|
| | Devon Rose | Matte Sand | Brownberry Creme |
| TiO2 suspension, Ex. 1 | 12.35 | 13.15 | 8.19 |
| Red 6 suspension | 4.60 | 0.64 | 2.15 |
| Red Iron Oxide, Ex. 2 | 1.24 | | 1.80 |
| Yellow 5 susp. | | 2.12 | |
| Black oxide | | | 1.48 |
| Bismuth pearl., Ex. 5 | 0.25 | | 0.07 |
| Blue susp., Ex. 3 | 0.40 | | |
| L red 7 susp. | 4.17 | | |
| Suspension base | 76.99 | 84.09 | 86.31 |
| Total | 100.00 | 100.00 | 100.00 |
| | Wild Plum | Sweet Honey | Coffee |
| TiO2 suspension, Ex. 1 | 1.96 | 5.11 | 6.03 |
| Red 6 suspension | | | 1.94 |
| Red Iron Oxide, Ex. 2 | | 1.22 | |
| Yellow 5 susp. | | 1.22 | 1.29 |
| Red 34 susp. | 1.88 | | |
| Black oxide | | 0.20 | 0.32 |
| D red 7 susp. | 19.32 | | |
| Bismuth pearl. susp., Ex. 5 | | 0.10 | |
| Blue susp., Ex. 3 | | 0.30 | |
| Suspension base | 76.84 | 91.85 | 90.42 |
| Total | 100.00 | 100.00 | 100.00 |
| | Crimson Creme | Creamy Pink | Sizzling Red |
| TiO2 suspension, Ex. 1 | 3.90 | 17.18 | 1.43 |
| Red 6 suspension | 20.24 | 4.94 | 14.52 |
| Yellow 5 susp. | | 0.49 | |
| D red 7 susp. | 14.39 | | |
| L red 7 susp. | | | 6.19 |
| Suspension base | 61.46 | 77.39 | 77.86 |
| Total | 99.99 | 100.00 | 100.00 |

TABLE 2

Analysis - Weight %

INGREDIENTS

| | Devon Rose | Matte Sand | Brownberry Creme |
|---|---|---|---|
| N-BUTYL ACETATE | 28.87 | 29.13 | 29.19 |
| ETHYL ACETATE | 11.30 | 10.93 | 11.28 |
| TOLUENE | 23.53 | 23.72 | 23.40 |
| DRY POLYESTER RESIN | 1.55 | 1.04 | 0.92 |
| BENZOPHENONE-1 | 0.12 | 0.13 | 0.13 |
| CAMPHOR | 1.91 | 2.00 | 1.97 |
| NITROCELLULOSE | 12.05 | 12.00 | 12.12 |
| STEARALKONIUM HECTORITE | 1.10 | 1.13 | 1.13 |
| DIBUTYL PHTHALATE | 6.41 | 6.46 | 6.46 |
| ISOPROPYL ALCOHOL | 5.24 | 5.33 | 5.38 |
| BISMUTH OXYCHLORIDE | 0.06 | | 0.02 |
| TITANIUM DIOXIDE | 1.13 | 1.21 | 0.75 |
| D&C RED #6 BARIUM LAKE | 0.23 | 0.03 | 0.11 |
| D&C RED #7 CALCIUM LAKE | 0.19 | | |
| D&C YELLOW #5 ALUMINUM LAKE | | 0.10 | |
| BLACK IRON OXIDE | | | 0.07 |
| RED IRON OXIDE | 0.08 | | 0.12 |
| IRON BLUE | 0.01 | | |
| TOL SULFONAMIDE\FORMALDEHYDE | 6.21 | 6.78 | 6.96 |
| TOTAL | 99.99 | 99.99 | 100.01 |

| | Wild Plum | Sweet Honey | Coffee |
|---|---|---|---|
| N-BUTYL ACETATE | 28.93 | 29.51 | 29.45 |
| ETHYL ACETATE | 11.07 | 11.27 | 11.16 |
| TOLUENE | 24.04 | 23.37 | 23.55 |
| DRY POLYESTER RESIN | 1.56 | 0.55 | 0.64 |
| BENZOPHENONE-1 | 0.13 | 0.13 | 0.13 |
| CAMPHOR | 1.83 | 2.00 | 2.01 |
| NITROCELLULOSE | 12.13 | 12.10 | 12.08 |
| STEARALKONIUM HECTORITE | 1.12 | 1.14 | 1.14 |
| DIBUTYL PHTHALATE | 6.47 | 6.49 | 6.50 |
| ISOPROPYL ALCOHOL | 5.28 | 5.38 | 5.34 |
| BISMUTH OXYCHLORIDE | | 0.02 | |
| TITANIUM DIOXIDE | 0.18 | 0.47 | 0.55 |
| D&C RED #6 BARIUM LAKE | | | 0.10 |
| D&C RED #34 CALCIUM LAKE | 0.08 | | |
| D&C RED #7 CALCIUM LAKE | 0.98 | | |
| D&C YELLOW #5 ALUMINUM LAKE | | 0.06 | 0.06 |
| BLACK IRON OXIDE | | 0.01 | 0.02 |
| RED IRON OXIDE | | 0.08 | |
| IRON BLUE | | 0.01 | |
| TOL SULFONAMIDE\FORMALDEHYDE | 6.19 | 7.40 | 7.29 |
| TOTAL | 99.99 | 99.99 | 100.02 |

| | Crimson Creme | Creamy Pink | Sizzling Red |
|---|---|---|---|
| N-BUTYL ACETATE | 28.12 | 28.76 | 28.98 |
| ETHYL ACETATE | 10.42 | 10.76 | 11.52 |
| TOLUENE | 24.84 | 23.97 | 23.66 |
| DRY POLYESTER RESIN | 2.59 | 1.47 | 1.53 |
| BENZOPHENONE-1 | 0.13 | 0.13 | 0.12 |
| CAMPHOR | 1.87 | 1.98 | 1.91 |
| NITROCELLULOSE | 12.13 | 12.01 | 12.12 |
| STEARALKONIUM HECTORITE | 1.11 | 1.12 | 1.10 |
| DIBUTYL PHTHALATE | 6.42 | 6.43 | 6.46 |
| ISOPROPYL ALCOHOL | 5.33 | 5.29 | 5.18 |
| BISMUTH OXYCHLORIDE | | | |
| TITANIUM DIOXIDE | 0.36 | 1.58 | 0.13 |
| D&C RED #6 BARIUM LAKE | 1.00 | 0.24 | 0.72 |
| D&C RED #7 CALCIUM LAKE | 0.73 | | 0.29 |
| D&C YELLOW #5 ALUMINUM LAKE | | 0.02 | |
| TOL SULFONAMIDE\FORMALDEHYDE | 4.95 | 6.24 | 6.28 |
| TOTAL | 100.00 | 100.00 | 100.00 |

These nine nail polish formulations were carefully tested, and found to exhibit the following qualities:

Better suspension in a centrifuge.

Higher gloss.

Less syneresis.

Higher hiding.

No hydrogen build up.

Better brushability and flowability.

Furthermore, less Bentone was needed to achieve the same suspension characteristics, implying that the inventive products would show less gellation, or viscosity build up on the shelf.

While illustrative embodiments of the invention have been described above, it is, of course, understood that various modifications will be apparent to those of ordinary skill in the art. Such modifications are within the spirit and scope of the invention, which is limited and defined only by the appended claims.

I claim:

1. A method of preparing a coated pigment material to improve the suspensibility of said pigment material in a nail enamel suspension, said nail enamel suspension having improved stability as a result of said pretreatment, said method comprising pre-treating pigment material, prior to grinding, in the following steps:

a) forming a coating mix by mixing uncoated pigment material with from 0.25 to 20 weight % based on said pigment material of a hydrophobic pigment coating mixture and with from one-third to ten times the weight of said pigment material of an organic hydrophobic pigment paste solvent, said hydrophobic pigment coating mixture comprising:

i) one part of a hydrophobic carboxylic acid having from 3 to 18 carbon atoms;

ii) from 0.1 to 10 parts by weight of a non-toxic carboxylic acid metal salt also having from 3 to 18 carbon atoms; and iii) from 0.5 to 10.0 parts based on the combined weight of said acid and said acid salt of a pigment-coating carrier resin; and b) aging said coating mix for from about 5 to about 30 hours, being time sufficient to coat said pigment material with said hydrophobic pigment coating mixture and provide good stability of a nail enamel suspension incorporating said coated pigment material.

2. A method according to claim 1 wherein said carrier resin is selected from the group consisting of an acrylates copolymer; a urethane elastomer; a non-oxidizing alkyd resin; a polyester resin; a hydrocarbon resin; a toluene sulfonamide formaldehyde resin and mixtures thereof.

3. A method according to claim 1 comprising mixing said pigment coating mixture with said pigment material in a proportion of from 0.25 to 20 weight % based on said pigment material in the presence of from one-third to ten times the weight of said pigment of said organic hydrophobic pigment paste solvent.

4. A method according to claim 1 wherein said pigment-coating mix is aged from 12 to 24 hours.

5. A method according to claim 1 including mixing said pigment-coating mix during aging.

6. A method according to claim 1, wherein said carrier resin binds said carboxylic acid and said non-toxic carboxylic acid metal salt to said pigment material as a result of aging said grinding mix.

7. A method according to claim 1 wherein the proportion of said non-toxic carboxylic acid metal salt is from 0.75 to 1.5 and of said pigment-coating carrier resin is from 0.75 to 1.2.

8. A method according to claim 1 wherein said carrier resin constitutes a weight amount on the same order of magnitude as said fatty acid and metal salt combined.

9. A method according to claim 1 wherein said metal of said non-toxic carboxylic acid metal salt is selected from the group consisting of sodium, potassium and calcium, and said carboxylic acid metal salt is soluble in said organic hydrophobic pigment paste solvent.

10. A method according to claim 1 wherein said hydrophobic carboxylic acid is octoic acid.

11. A method according to claim 1 wherein said carboxylic acid salt is an octoate.

12. A method according to claim 1 wherein said solvent is selected from the group consisting of toluene, n-butyl acetate, ethyl acetate and mixtures thereof.

13. A method of preparing a pigment paste grinding mix comprising adding nitrocellulose and a film-forming resin to an aged coating mix produced by the method of claim 1 and milling the resultant grinding mix.

14. A method according to claim 13 wherein said milling is sufficient to achieve a fineness of at least 8+ on the Hegman scale.

15. A method of manufacturing a nail enamel composition comprising incorporating a coated pigment material according to claim 1 in a nail enamel composition, after grinding said coated pigment material.

* * * * *